United States Patent [19]

Hagen et al.

[11] Patent Number: 5,783,694

[45] Date of Patent: Jul. 21, 1998

[54] IR-ABSORBING PHTHALOCYANINES

[75] Inventors: Helmut Hagen, Frankenthal; Bernhard Albert, Forst, both of Germany

[73] Assignee: BASF Aktiengesellschaft, Ludwigshafen, Germany

[21] Appl. No.: 823,368

[22] Filed: Mar. 24, 1997

[30] Foreign Application Priority Data

Apr. 2, 1996 [DE] Germany ............... 196 13 139.1

[51] Int. Cl.[6] ............... C07D 487/22; C09B 47/20; F21V 9/04

[52] U.S. Cl. ............... 540/123; 540/122; 540/124; 540/125; 540/127; 252/587

[58] Field of Search ............... 540/122, 123, 540/124, 125, 139, 140, 127

[56] References Cited

U.S. PATENT DOCUMENTS 5,322,760  6/1994  Itoh et al. ............... 540/126
5,705,101  1/1998  Oi et al. ............... 252/587

FOREIGN PATENT DOCUMENTS 0 155 780  9/1985  European Pat. Off. .

*Primary Examiner*—Mukund J. Sham
*Assistant Examiner*—Pavanaram K. Sripada
*Attorney, Agent, or Firm*—Oblon, Spivak, McClelland, Maier & Neustadt, P.C.

[57] ABSTRACT

Compounds of the general formula I

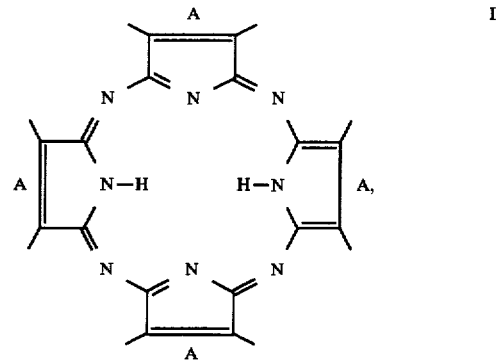

where the A radicals are, independently of one another,

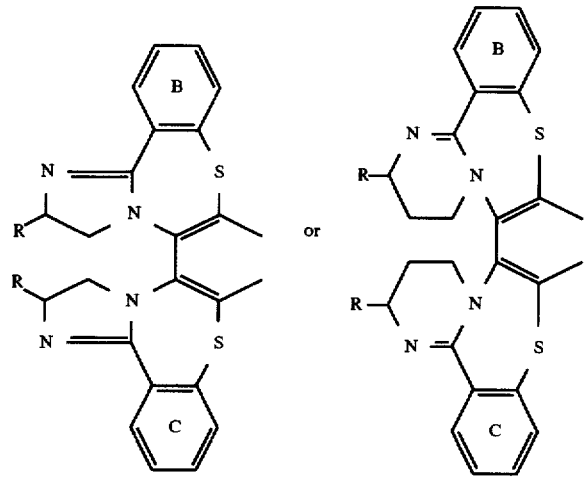

where the rings B and C can also, independently of one another, be substituted by $C_1$–$C_4$-alkyl, $C_1$–$C_4$-alkoxy, nitro, hydroxysulfonyl, benzoyl or a fused-on benzo ring, R is hydrogen or methyl, and the two hydrogen atoms on the nitrogens can be replaced by copper, nickel, vanadyl, magnesium, AlCl or zinc, are suitable as IR-absorbers.

5 Claims, No Drawings

IR-ABSORBING PHTHALOCYANINES

The invention relates to compounds of the formula I

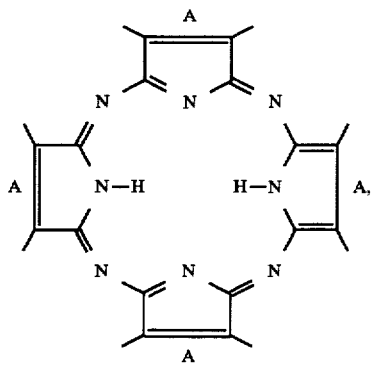

where the A radicals are, independently of one another,

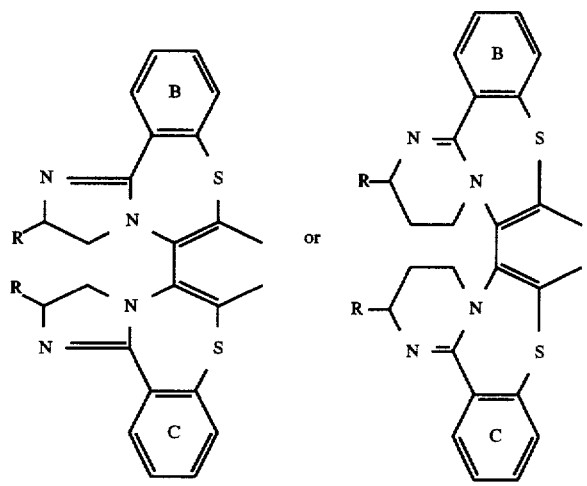

where the rings

B and C can also, independently of one another, be substituted by $C_1$-$C_4$-alkyl, $C_1$-$C_4$-alkoxy, nitro, hydroxysulfonyl, benzoyl or a fused-on benzo ring, R is hydrogen or methyl, and the two hydrogen atoms on the nitrogens can be replaced by copper, nickel, vanadyl, magnesium, AlCl or zinc.

R is preferably hydrogen. Also preferred are unsubstituted rings B and C or rings which are substituted by nitro, methoxy or hydroxysulfonyl, and benzo-fused rings.

Preferred central atoms for the phthalocyanines according to the invention are Cu and Ni.

Compounds of the formula I can be prepared by reacting compounds of the formulae IIa and/or IIb

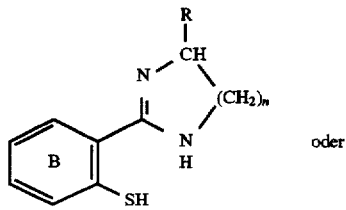 oder

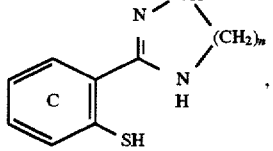

where n is, independently of one another, 1 or 2, and R has the stated meaning, with halogen-substituted (preferably 16 halogen atoms) phthalocyanines. Details of the reaction can be found in the examples in which, unless noted otherwise, data in parts and percentages are based on weight.

European Patent 155 780 has disclosed phthalocyanines which have sulfur and/or nitrogen substituents; they are obtained by reacting halogen-substituted phthalocyanines with thiophenols or aminothiophenols.

It is surprising that compounds of the formulae IIa and IIb can also be reacted with halophthalocyanines and lead to phthalocyanines which absorb in a wavelength range from 720 to 1100 μm.

Because of the very efficient absorption, the compounds according to the invention are suitable for all purposes in which such absorption is desired, for example in IR-absorbing (printing) inks, plastics (eg. spectacles or sheets for agriculture, film-laminated windscreens and windows) or as absorbers in the laser transfer of dyes in thermotransfer printing.

It is furthermore possible to use them to produce IR-readable barcodes or markings on currency notes and securities functioning as security systems.

EXAMPLE 1

35.6 g (0.2 Mol) of 2-mercaptophenylimidazoline and 13.5 g of powdered potassium hydroxide are stirred in 100 ml of N-methylpyrrolidone at 120° C. for 10 minutes. Then, at the same temperature, 11.5 g of Cu phthalocyanine substituted with 15–16 chlorine atoms are added and the mixture is stirred at 130° C. for a further 20 hours. It is subsequently cooled, filtered to remove precipitated salt (KCl and a little CuCl) and distilled under reduced pressure to remove the solvent. The distillation residue is dissolved in hot alcohol, filtered and mixed with ethyl acetate. After cooling, 17 g of a grayish brown compound which, according to elemental analysis and spectroscopic data, has the formula indicated below are obtained.

The yield corresponds to 86% of theory based on Cu phthalocyanine.

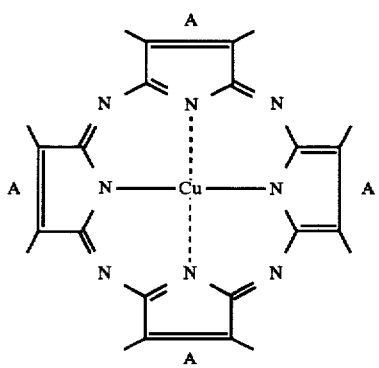

A = 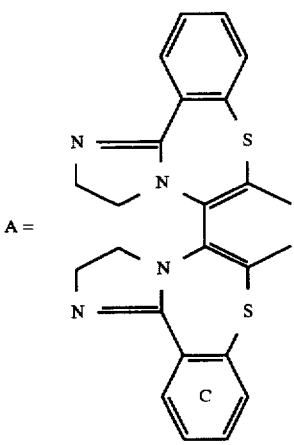

A = 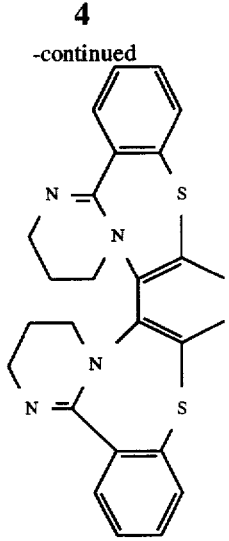

EXAMPLE 2

38.4 g (0.2 Mol) of 2-mercaptophenyl-3,4,5,6-tetrahydropyrimidine and 13.5 g of powdered potassium hydroxide are stirred in 100 ml of N-methylpyrrolidone at 120° C. for 30 minutes. After adding 11.5 g of the perchlorinated Cu phthalocyanine, the mixture is stirred at 120°–130° C. for 20 hours. After cooling, it is filtered and the solvent is removed under reduced pressure. The distillation residue is dissolved in hot alcohol, filtered, mixed with ethyl acetate and cooled. The precipitate is filtered off with suction and washed with water. Drying results in 16.5 g (79% of theory) of a greenish black Cu phthalocyanine of the formula

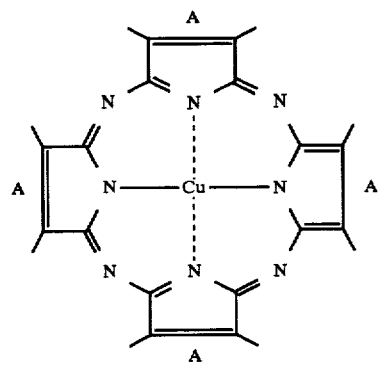

When a mixture of compounds of the formulae IIa (n=1, R=H) and IIb (n=2, R=H), the rings B and/or C not being substituted further, is used in the reaction of the perhalogenated Cu phthalocyanine, a product with similar properties is obtained.

Use Example 5 g of the compound from Example 1 were shaken mechanically with 50 g of glass beads in 100 ml of ethanol and 15 g of polyvinyl acetate for 2 hours.

The mixture was applied with a knife to a polyester sheet and, after drying, provided a homogeneous layer which had an absorption maximum at 780 nm.

We claim:

1. A compound of the formula I

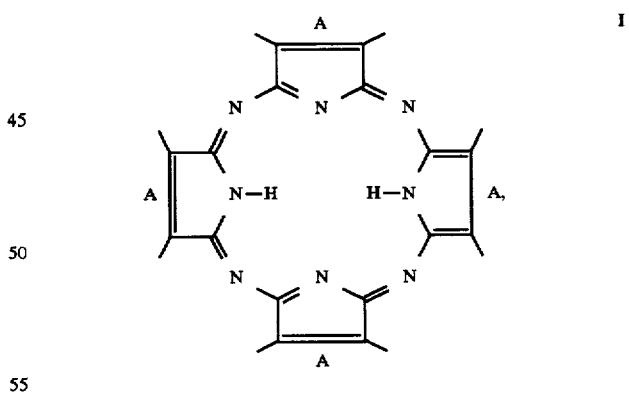

where the A radicals are, independently of one another,

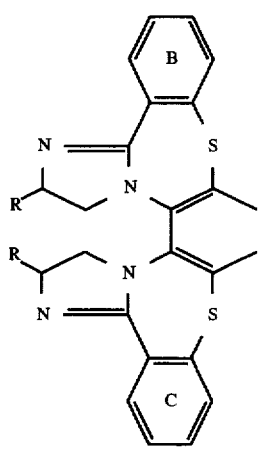 or 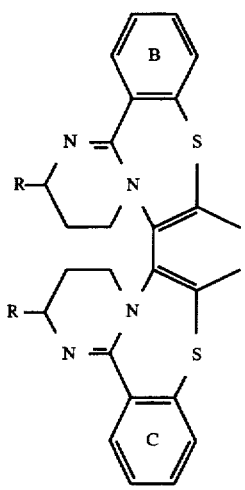

where the rings

B and C can also, independently of one another, be substituted by $C_1$–$C_4$-alkyl, $C_1$–$C_4$-alkoxy, nitro, hydroxysulfonyl, benzoyl or a fused-on benzo ring, R is hydrogen or methyl, and the two hydrogen atoms on the nitrogens can be replaced by copper, nickel, vanadyl, magnesium, AlCl or zinc.

2. A compound as claimed in claim 1, where R is hydrogen.

3. A compound as claimed in claim 1, where the rings B and C are substituted by nitro, methoxy or hydroxysulfonyl, are benzo-fused or are unsubstituted.

4. A compound as claimed in claim 1, where the central atom is Cu or Ni.

5. Method of using a compound as claimed in claim 1 for IR absorption.

* * * * *